United States Patent
Kraemer et al.

(10) Patent No.: US 6,343,906 B1
(45) Date of Patent: Feb. 5, 2002

(54) ARRANGEMENT FOR TRANSPORTING MICROTITRATION PLATES IN AN AUTOMATIC HANDLING MACHINE

(75) Inventors: Wolfgang Kraemer, Jena; Thomas Moore, Drackendorf Stadt Jena; Heiko Oehme, Jena; Georg Schmidt, Wuppertal; Ralph Noll, Mettmann; Martin Bechem, Wuppertal, all of (DE)

(73) Assignee: CyBio Instruments GmbH, Jena (DE)

( * ) Notice: Subject to any disclaimer, the term of this patent is extended or adjusted under 35 U.S.C. 154(b) by 0 days.

(21) Appl. No.: 09/442,563

(22) Filed: Nov. 18, 1999

(30) Foreign Application Priority Data

Nov. 18, 1998 (DE) .......................................... 198 54 002

(51) Int. Cl.⁷ .......................... B65G 47/82; G01N 35/04
(52) U.S. Cl. .................... 414/399; 414/398; 198/345.3; 198/463.3; 198/468.01; 198/578
(58) Field of Search ................................ 414/373, 389, 414/398, 399, 401, 402; 198/345.3, 463.3, 465.1, 468.01, 468.2, 468.6, 469.1, 470.1, 570, 578

(56) References Cited

U.S. PATENT DOCUMENTS

| | | | | |
|---|---|---|---|---|
| 4,147,294 A | * | 4/1979 | Davidson et al. | 494/20 |
| 4,275,983 A | * | 6/1981 | Bergman | 414/676 |
| 4,373,840 A | * | 2/1983 | Miller | 198/346.1 |
| 4,539,479 A | * | 9/1985 | Sheets et al. | 250/491.1 |
| 4,764,076 A | * | 8/1988 | Layman et al. | 414/217 |
| 4,836,354 A | * | 6/1989 | Motoda | 198/345.3 |
| 5,149,654 A | * | 9/1992 | Gross et al. | 435/303.1 |
| 5,273,718 A | * | 12/1993 | Skold et al. | 422/101 |
| 5,339,940 A | * | 8/1994 | Simms | 198/345.3 |
| 5,372,471 A | * | 12/1994 | Wu | 414/806 |
| 5,460,057 A | * | 10/1995 | Ostrup | 73/864.81 |
| 5,579,695 A | * | 12/1996 | Cockayne | 104/140 |
| 5,873,453 A | | 2/1999 | Vetter | |

FOREIGN PATENT DOCUMENTS

| | | | |
|---|---|---|---|
| DE | 43 29 791 | * | 3/1995 |
| EP | 0756995 | | 2/1997 |
| JP | 06 0088830 | | 3/1994 |

* cited by examiner

Primary Examiner—Robert P. Olszewski
Assistant Examiner—Gerald J. O'Connor
(74) Attorney, Agent, or Firm—Reed Smith LLP

(57) ABSTRACT

An arrangement for transporting microtitration plates in an automatic handling machine is disclosed comprising at least one linear-transport device on which a carriage, which has at least one place of deposit for a microtitration plate, is transported in a straight line, under automatic control, between two limit positions. A lifting device is included with vertically displaceable bolts by which the microtitration plates can be lifted off or deposited on the carriage. At least one rotary device is also included in which a rotary element which has at least one resting place for a microtitration plate can be moved, under automatic control, about a fixed rotation shaft. The rotary device is designed and arranged in such a way with respect to the linear-transport device that the resting place can be rotated between the place of deposit and the microtitration plate which has been lifted and is resting on the bolts, so that the surface centers of gravity of the place of deposit of the resting place and of the microtitration plate lie on a line which is parallel to the bolts.

5 Claims, 8 Drawing Sheets

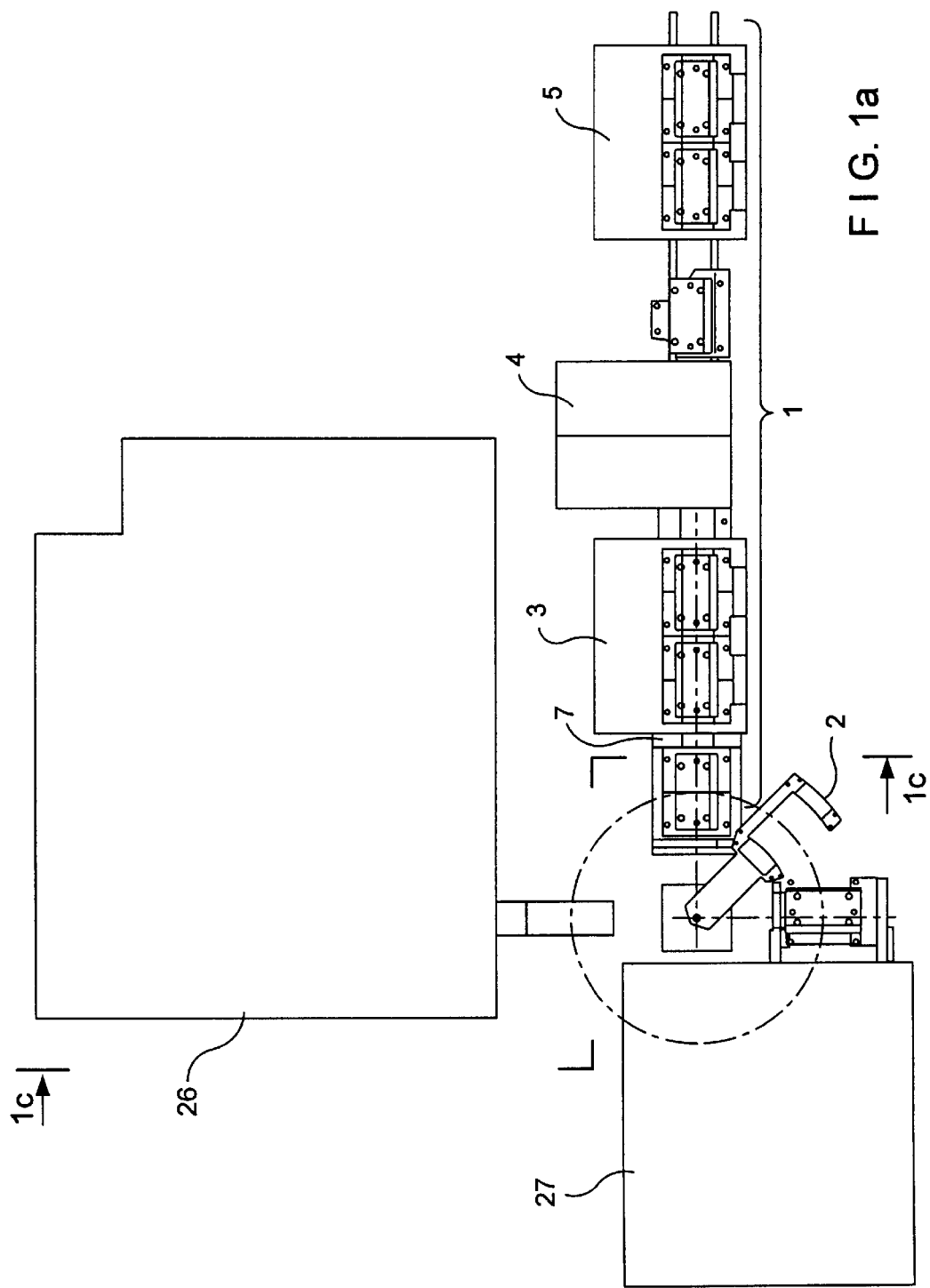

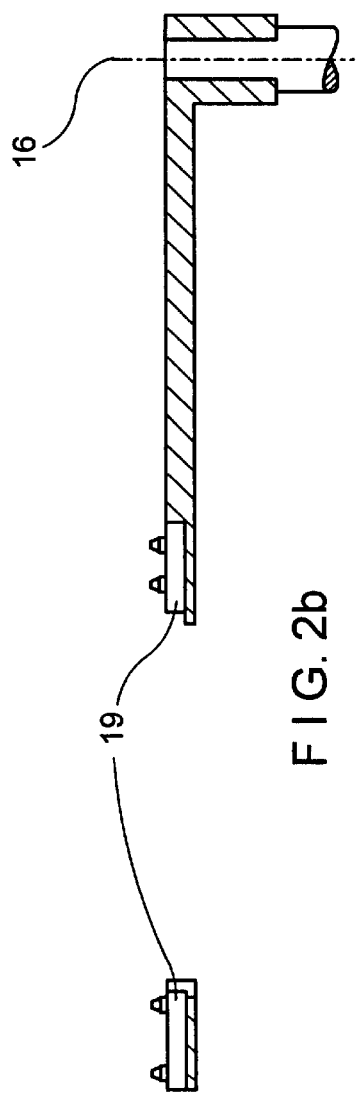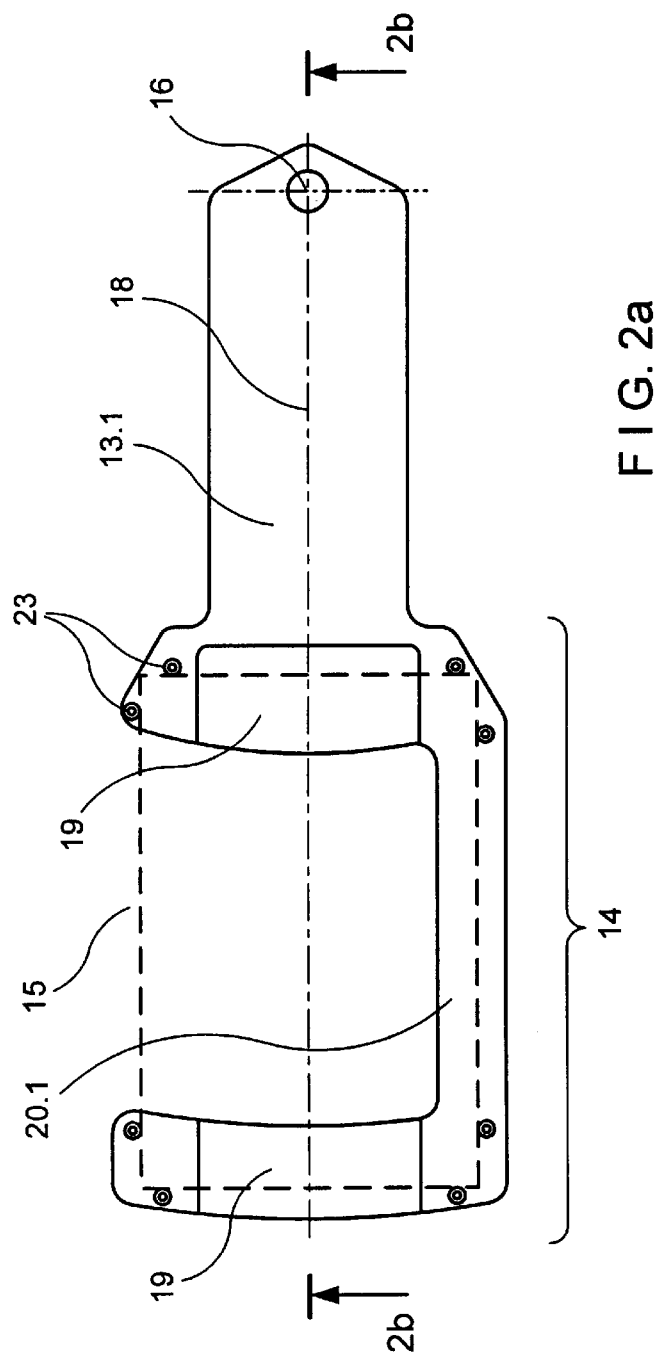

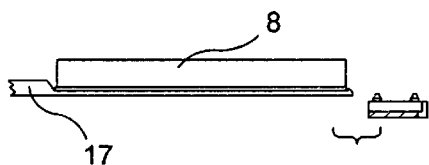
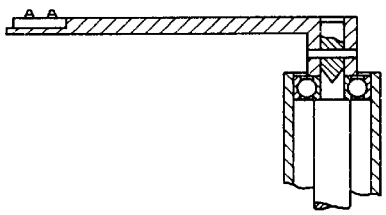
F I G. 4a
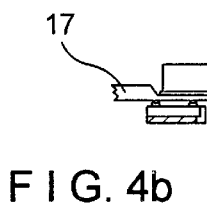
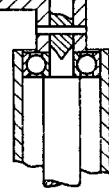
F I G. 4b
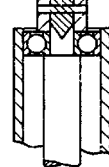
F I G. 4c
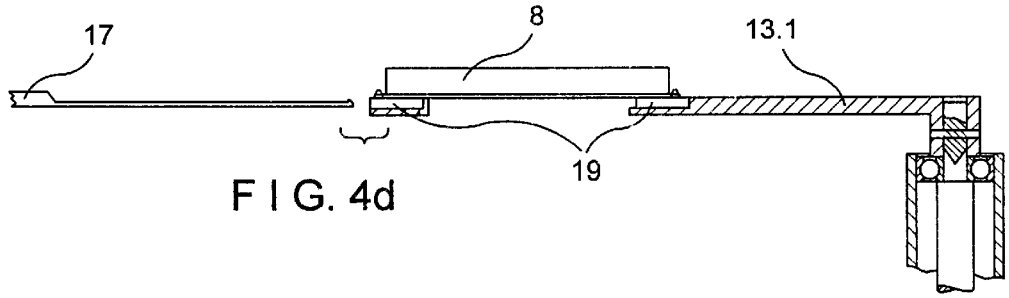
F I G. 4d
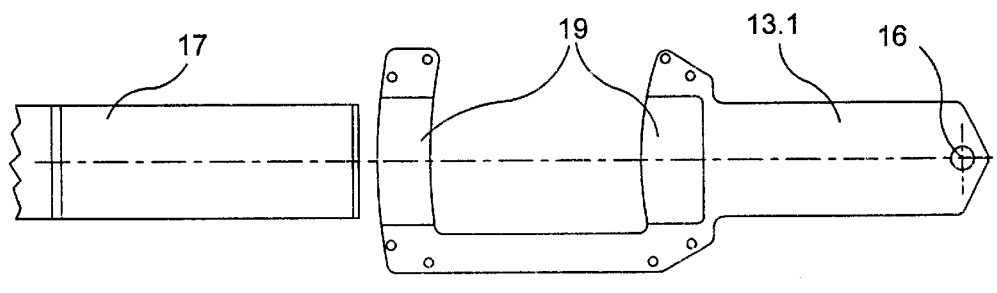
F I G. 4e

ARRANGEMENT FOR TRANSPORTING MICROTITRATION PLATES IN AN AUTOMATIC HANDLING MACHINE

BACKGROUND OF THE INVENTION a) Field of the Invention

An automatic handling machine for microtitration plates is to be understood in the broadest sense as meaning an arrangement of various devices and appliances which are connected to one another via a transport arrangement, by means of which the microtitration plates are supplied to the individual devices and appliances (referred to below as work stations) in an order which is determined by the preset process sequence.

b) Description of the Related Art

In addition to the microtitration plates, it is necessary, for example, to move vessels for cultures, nutrient media, buffers, reagents, dissolved substances and washing liquids. The devices and appliances may, for example, be: washing devices, metering devices, stackers, suction devices, microtitration plate stores with optional access (so-called hotels), incubators (with heating and/or cooling), measurement devices (photometers, luminometers, units for measuring fluorescence, nephelometers), cooling and heating devices (e.g. thermocyclers), mixers, magnetic-particle handling devices.

At various workstations, e.g. the metering device, the corresponding operation can be performed without the microtitration plate having to be taken off the transport arrangement. At other workstations, e.g. an incubator or a stacking device, it is necessary to remove the microtitration plate from the transport arrangement.

An automatic handling machine with a transport arrangement in which a carriage can be moved to and fro in a straight line, on two parallel rails of a carriage guide, between two limit positions is known in practice. The individual workstations are arranged on or above the transport arrangement, in a sequence corresponding to that of the process. On the carriage, there are advantageously a plurality of places of deposit, on which the microtitration plates are deposited next to one another in a defined order. The defined order of depositing may, for example, be achieved by means of a centering pin arrangement on each of the places of deposit, which describes the periphery of the microtitration plate.

At the workstations at which it is necessary to remove the microtitration plate from the transport device, a lifting device is arranged under the carriage guide. This lifting device engages, by means of four bolts which are guided parallel to one another, between the rails, through openings which are provided for this purpose in the carriage, on the bottom of the microtitration plate and lifts the latter off the place of deposit. The four bolts are arranged in such a manner with respect to one another and with respect to the microtitration plate resting on the carriage that the surface center of gravity of the microtitration plate lies in the quadrilateral which the four bolts form. In the lifted position, the microtitration plate can be removed, for example by a gripper or a loading arm.

By way of example, there are incubators in which the microtitration plates are automatically conveyed into the inner chamber and out of this chamber by means of a loading arm which belongs to the incubator and is similar to a cake-slice. On the loading arm, there may be centering elements which prevent the microtitration plate from slipping on the loading arm when the latter is moved.

To allow the microtitration plate to be deposited on and picked up from a bearing surface in the interior of the incubator, there has to be a cutout, into which the loading arm fits, in the plane of the bearing surface. If the microtitration plate is picked up from and deposited on the carriage directly, a corresponding cutout has to be provided in the carriage as well. The transfer between the transport device and the loading arm is easier if, as described above, the microtitration plate is lifted off the carriage by means of a lifting device. The loading arm is then narrower than the distance between the bolts and only has to be moveable in a single plane.

Many measurement appliances have an appliance carriage which can be displaced in two coordinates and is able to move the microtitration plate within the fixed measurement-beam path, so that all the cavities in the microtitration plate can be measured.

The transfer between the transport arrangement and the appliance carriage may either be carried out by a gripper picking up the microtitration plate from the carriage and depositing it on the appliance carriage or vice versa, or by the microtitration plate being lifted in the manner described and the appliance carriage, which in this case is designed as a frame which is open on one side, moving in under the lifted microtitration plate, which is then deposited as the lifting device is lowered.

For complex tasks to be performed by the automatic handling machines, the linear arrangement of the workstations on the transport arrangement results in arrangements of appliances which take up very large amounts of space. If a plurality of microtitration plates are transported simultaneously on the carriage in the automatic handling machine, the workstations have to be arranged in succession in accordance with the process sequence. For example, there may be a need for a plurality of rinsing devices if the "rinsing" step has to be repeated a number of times in the process sequence. Although in this case the process sequences for a plurality of microtitration plates may partially overlap in time, the common transport means that the step which lasts the longest is the determining factor for the total operating time.

By contrast, if there is only one microtitration plate in the automatic handling machine, although it is possible to approach workstations a number of times by means of transport in two directions, the total operating time becomes even slower, since the process sequences for the individual microtitration plates always have to take place one after the other in terms of time.

A further disadvantage is that changes in the process sequence result in unnecessarily long transport paths, since the workstations are then no longer approached in the order in which they are arranged.

OBJECT AND SUMMARY OF THE INVENTION

The invention is based on the object of providing, taking into account the known transport arrangement and lifting device, a novel arrangement for transporting microtitration plates which makes it possible to move a plurality of microtitration plates independently of one another and overlapping one another in terms of time and which allows a flexible operating regime with short transport paths.

The transfer of the microtitration plates within the transport device and between the transport device and various transport means, such as the loading arm of an appliance or an appliance carriage, is to be achievable using simple sequences of movements.

According to the invention, this object is achieved, for an arrangement for transporting microtitration plates, in an automatic handling machine comprising at least one linear-transport device on which a carriage, which has at least one place of deposit for a microtitration plate, is transported in a straight line, under automatic control, between two limit positions. A lifting device is included with vertically displaceable bolts by which the microtitration plates can be lifted off or deposited on the carriage. At least one rotary device is also included in which a rotary element which has at least one resting place for a microtitration plate can be moved, under automatic control, about a fixed rotation shaft. The rotary device is designed and arranged in such a way with respect to the linear-transport device that the resting place can be rotated between the place of deposit and the microtitration plate which has been lifted and is resting on the bolts, so that the surface centers of gravity of the place of deposit of the resting place and of the microtitration plate lie on a line which is parallel to the bolts.

According to the invention, the arrangement for transporting microtitration plates comprises a linear-transport device 1 and at least one rotary device 2. The arrangement of the individual workstations with respect to one another and with respect to the transport arrangement fixes the length of the transport path between the individual workstations. Workstations which during the process sequence have to be approached selectively or even a number of times by the same microtitration plate are advantageously distributed around a rotary device 2. The rotary device 2 may also serve to connect a plurality of linear-transport devices 1. Also, rotary devices 2 may be arranged on both sides of the linear-transport device 1. Appliances which in the process sequence are always approached in succession by a microtitration plate are advantageously arranged next to one another, in this order, along a linear- transport device 1. The rotary device 2 and the linear-transport device 1 can be controlled independently of one another, so that at least two microtitration plates can independently approach workstations at the same time.

The invention is to be explained below with reference to the drawings.

BRIEF DESCRIPTION OF THE DRAWINGS

In the drawings:

FIGS. 1a–c show a structure of an automatic handling machine for microtitration plates, having a rotary device and a linear-transport device;

FIGS. 2a–b show an exemplary embodiment of a rotary arm, in plan view and sectional illustration;

FIGS. 4 to 4e show the transfer of a microtitration plate from the loading arm of an appliance to the rotary arm.

DESCRIPTION OF THE PREFERRED EMBODIMENTS

Figure 1B:
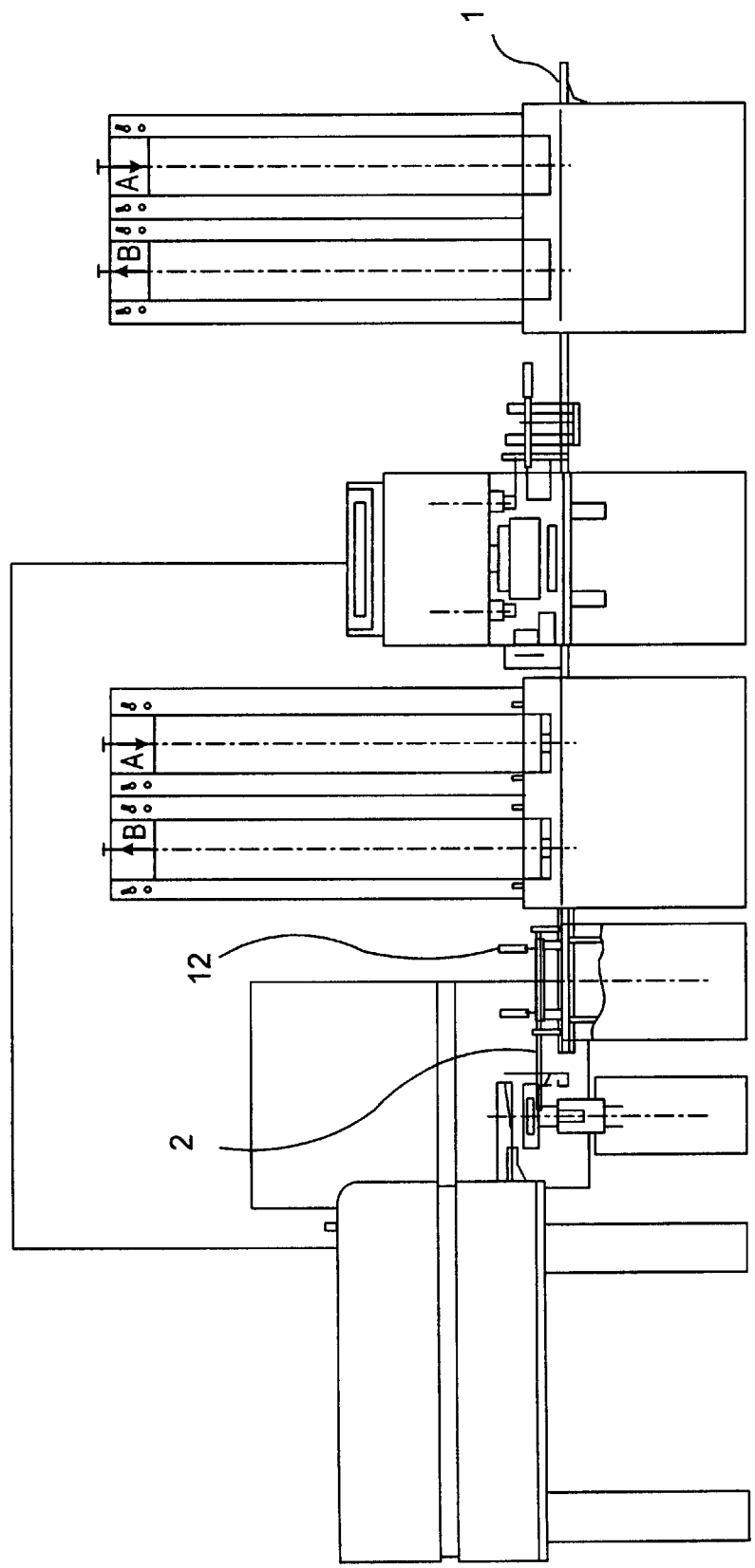
Figure 1C:
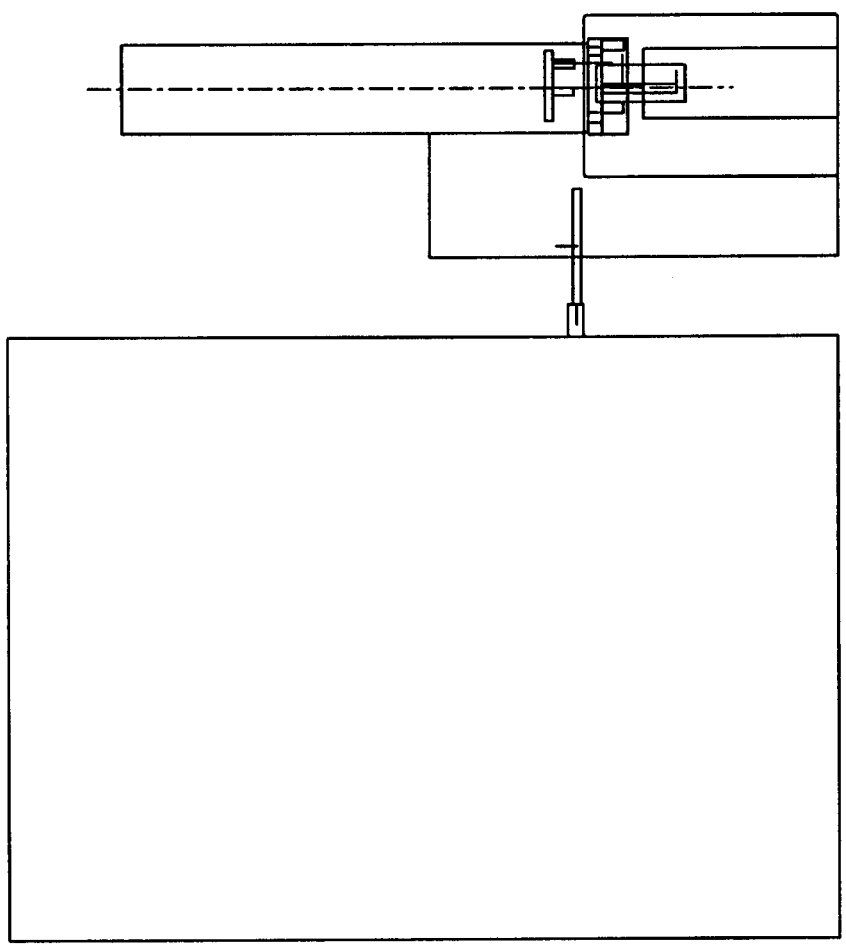

FIGS. 1a–c show a structure of an automatic handling machine having a linear- transport device 1, a rotary device 2, a lifting device 12 and various workstations, in three different views.

The linear-transport device 1 essentially comprises two parallel guide rails which are attached to a laterally arranged frame, so that the individual workstations can also be arranged above the linear-transport device 1, and the lifting device 12, as well as workstation- associated devices for lifting, can be arranged under the linear-transport device 1. In this exemplary embodiment, the workstations arranged along the linear-transport device 1 are to be a stacker 3, an automatic metering appliance 4 and a measurement appliance 5. A carriage 6 is moved to the individual workstations along the guide rails under automatic control; the workstations are arranged in such a manner with respect to one another and with respect to the transport device that the transport paths are as short as possible. Execution of the process sequence at the various workstations may require different positioning of the microtitration plate 8 (not shown in FIG. 1) with respect to the workstation. For example, microtitration plates 8 can be filled by means of the automatic metering appliance without the microtitration plate 8 having to be removed from the carriage 6.

It is expedient to arrange the delivery unit of the automatic metering appliance 4 in the same matrix as the microtitration plate 8 (8×12 or 16×24 grid). If small volumes are to be dispensed to the microtitration plate 8 from the automatic metering appliance 4, without liquid already being situated in the microtitration plate 8, it may under certain circumstances be necessary for the drop which leaves the pipette tip or needle of the automatic metering appliance 4 to come into contact with the bottom of the cavity in the microtitration plate 8. For this purpose, the microtitration plate 8 is raised to the required height by means of a lifting device.

By means of a slide arm which is able to transport a microtitration plate 8 transversely with respect to the direction of movement of the carriage 6, it is possible to remove microtitration plates 8 from the process or transfer them to other appliances. In exactly the same way, it is also possible to incorporate further microtitration plates 8. If microtitration plates 8 are to be stored, the plate which is resting on the carriage 6 is moved to under the shaft of the stacker 3. A lifting device 12 lifts the microtitration plate 8 off the carriage until it lifts up the plates which are resting on magnetic catches in the stacker shaft. The magnetic catches can then be retracted, and the stack of plates in the stacker shaft is then raised sufficiently far for the bottom plate to be above the magnetic catches. After the magnetic catches have been extended, the stack of plates can be deposited on the magnetic catches by being lowered. Removal is carried out in the reverse order. It is also possible to move the stacker shaft described above in a plane.

The linear-transport device 1 described above is known from the prior art. The innovation in this invention is that at one end there is a coupling point at which the microtitration plate 8 is transferred to a rotary device 2. At this coupling point, below the linear-transport device 1, there is a lifting device 12 which, as is known from the prior art, lifts the microtitration plate 8 off the carriage 6 located above it by means of extendable bolts 11. Workstation-associated devices for lifting may also be constructed in a similar way. FIGS. 3a–d show this lifting device 12 in its various operating positions. In the same way as in the prior art, the carriage 6 contains a plurality of places of deposit 7 on which the microtitration plates 8 are deposited in a defined position (one place of deposit 7 can be seen in FIG. 3b). The defined position is achieved by means of a first pin arrangement 9, which describes the periphery of the microtitration plate 8, on each of the places of deposit 7, between which pins the microtitration plate 8 is deposited. Furthermore, the carriage 6 has apertures 10, in a pattern corresponding to that of the bolts 11 of the lifting device 12, in the inner surface area between the first pin arrangements 9, so that the bolts 11 can be guided through the place of deposit 7, which is located above the lifting device 12, of the carriage 6 and onto the bottom of the microtitration plate 8, and the microtitration plate 8 is lifted as the bolts 11 are extended further.

Advantageously, the apertures 10 are larger than the diameter of the bolts, thus allowing a relative movement. The carriage 6 may also be designed as a frame, so that the bolts can be guided through without hindrance.

While the microtitration plate 8 is in the raised position, a rotary element 13 of the rotary device 2 is rotated under the microtitration plate 8. When the bolts 11 are then lowered, the microtitration plate 8 is deposited on the rotary element 13. The rotary element 13 is attached to a rotation shaft 16 which is able, independently of the control of the carriage 6, but likewise with automatic control, to move the rotary element 13 in both directions of rotation, as desired, in a single plane. An additional vertical displaceability of the rotation shaft 16 allows the transfer to take place at various levels.

Figure 1D:
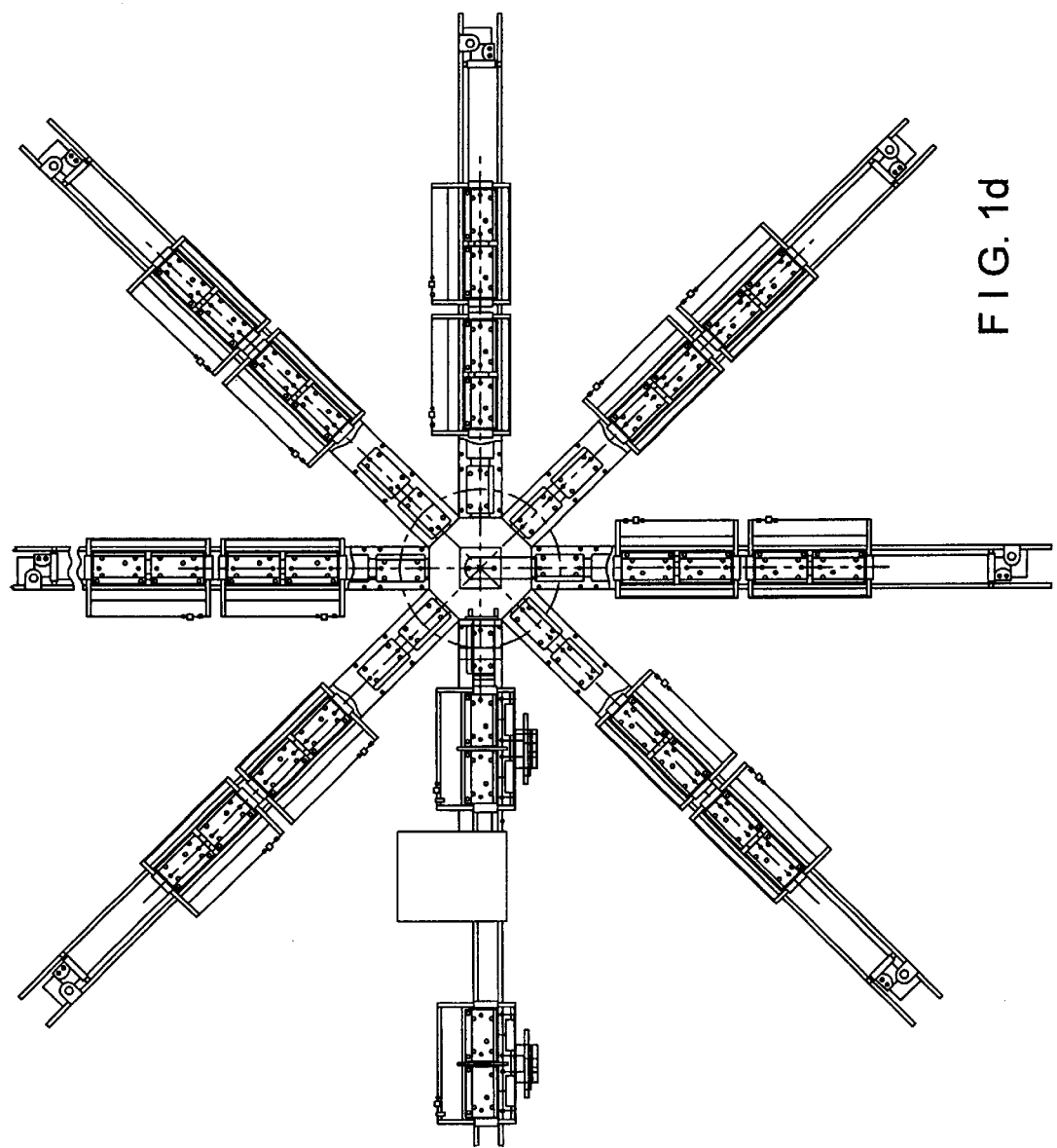
FIGS. 1d shows a structure of an automatic handling machine for microtitration plates, having a rotary device and a plurality of linear-transport devices which are arranged in the shape of a star.
Figure 3E:
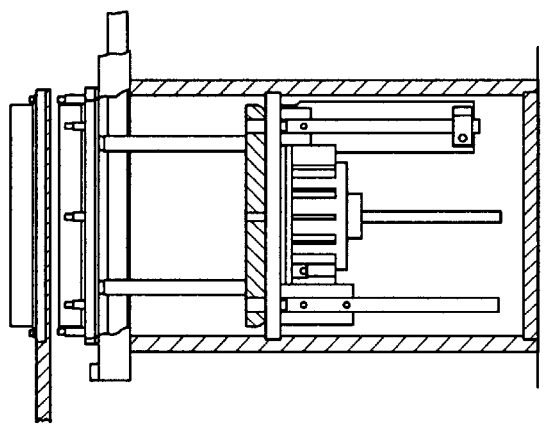
FIGS. 3a–e show the transfer of a microtitration plate from the carriage to the rotary arm, on the basis of showing the lifting device in different positions.
Figure 3C:
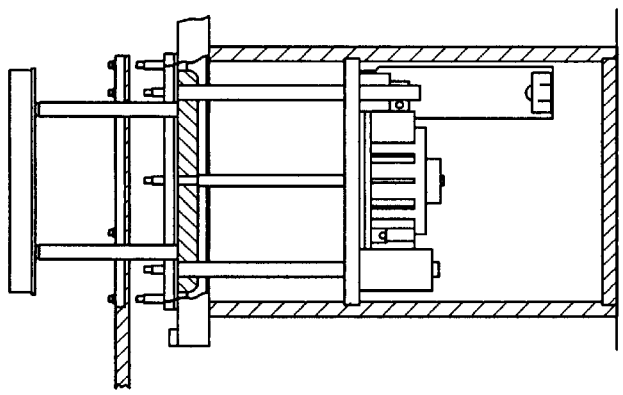
Figure 3D:
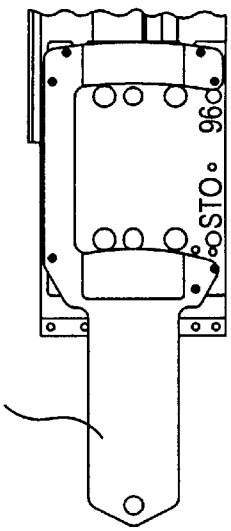
Figure 3A:
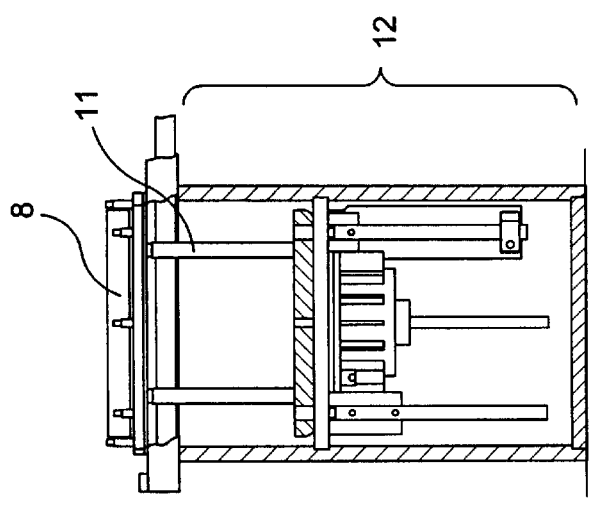
Figure 3B:
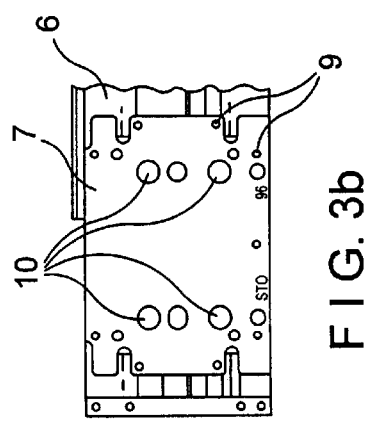

The arrangement of the workstations around the rotation shaft 16 of the rotary element 13 may be in the form of a star. Depending on the radius selected for the rotary element 13, it is possible to provide a different number of transfer points for workstations or, as in a further exemplary embodiment, which is illustrated in FIG. 1*d* but will not be explained in more detail, to provide a different number of coupling points to linear-transport devices 1. Naturally, a combination of the two variants is also possible.

In the first exemplary embodiment (FIGS. 1*a–d*), a measurement appliance 26 and an incubator 27 are arranged around the radius of movement of the rotary element 13.

The rotary element 13 of the rotary device 2 is a rotary arm 13.1. Such a rotary arm 13.1 is shown in FIGS. 2*a,b*. At its free end 14, this rotary arm 13.1 is of plate-like design, with external dimensions which are larger than those of a microtitration plate 8. In a similar manner to the first pin arrangement 9 on the places of deposit 7 of the carriage 6, there is a second pin arrangement 23 at the free end 14, so that the microtitration plate 8 is deposited in a defined position on the rotary arm 13.1 and the microtitration plate 8 remains securely in this position when the rotary arm 13.1 is accelerated. To allow the rotary arm 13.1 to be rotated under the microtitration plate 8 which has been lifted by the lifting device 12, the plate-like free end 14 has a recess 15 which is in the form of a jaw and is larger than the area taken up by the bolts 11. Advantageously, the lateral surfaces which delimit the jaw-shaped recess 15 are curved in the form of an arc, the center points of the respective arcs in each case lying in the rotation shaft 16 of the rotary arm 13.1. This allows the bolts 11 to be pivoted in without hindrance while providing the minimum possible surface area of the jaw-like recess 15, which is important for optimum dimensioning of the rotary arm 13.1. The microtitration plate 8 can be lifted off the rotary arm 13.1 constructed in this way by the lifting device 12, in a similar manner to the way in which it is lifted off the place of deposit 7 on the carriage 6, and can be deposited on the carriage 6 of the linear-transport device 1 or on an appliance carriage which belongs to a workstation. The microtitration plate 8 may also be removed from or placed onto the rotary arm 13.1 in the direction of the axis 18 of the rotary arm 13. 1, by means of a loading arm 17. The axis 18 of the rotary arm 13.1 is defined by the connection between the rotation shaft 16 and the surface center of gravity of the deposited microtitration plate 8. In order to be able to push the loading arm 17, which may be a thin flat plate, under the microtitration plate 8, the rotary arm 13.1 has an axially symmetrical first cutout 19, the lateral border of which can be used to guide the loading arm. FIGS. 4*a–e* show how the microtitration plate 8 is deposited on the rotary arm 13.1 by means of loading arm 17. The surface on which the microtitration plate 8 is deposited is to be referred to as first resting place 20.1.

As has been described, the rotary arm 13.1 allows the microtitration plate 8 to be removed or deposited by means of the lifting device 12, a workstation-associated device of the same type for lifting, or a loading arm 17. In this way, the transport arrangement can be adapted more easily to different workstations.

Figure 5:
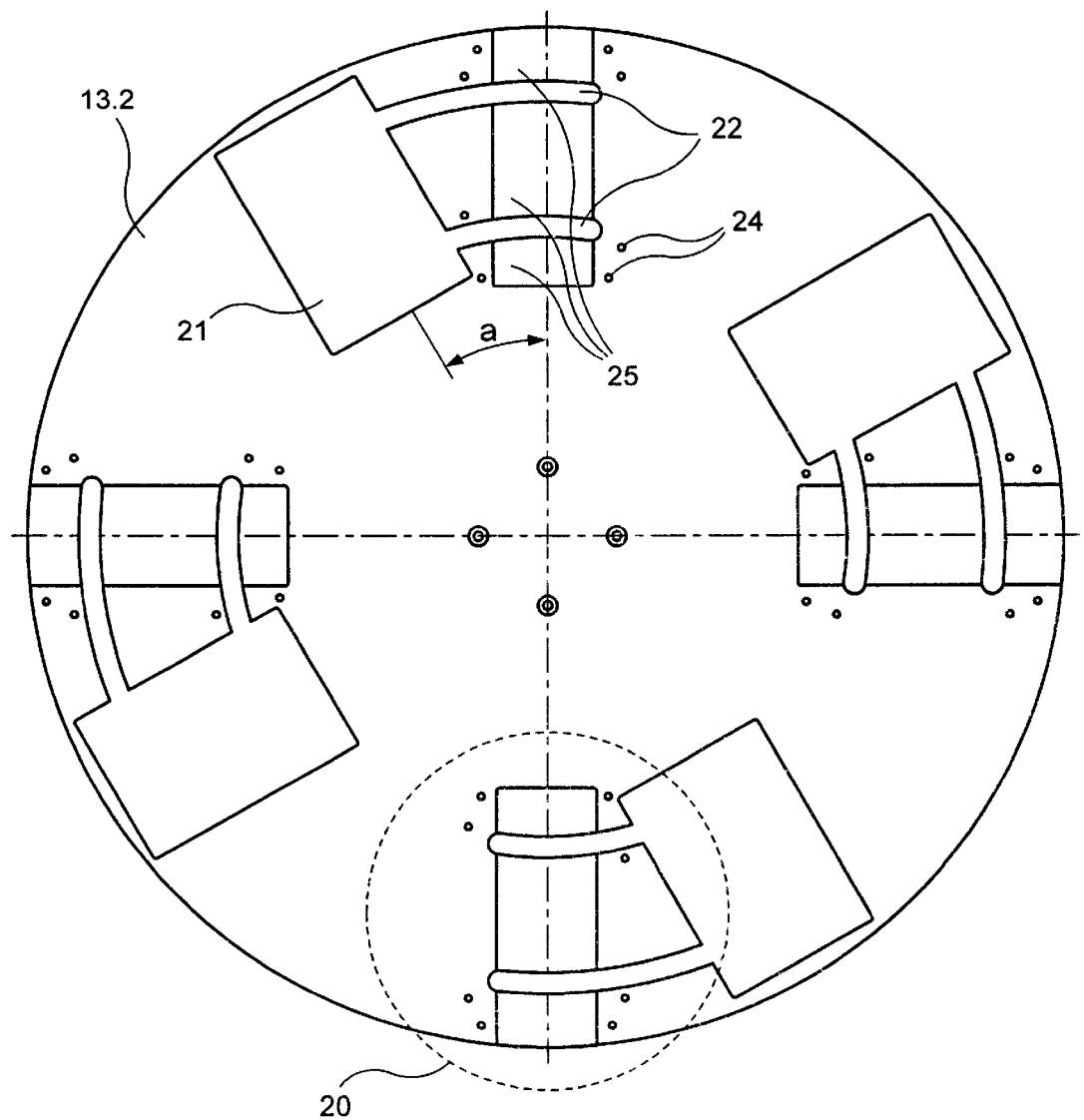
FIG. 5 shows an exemplary embodiment of a rotary wheel for holding a plurality of microtitration plates.

In a second exemplary embodiment, the rotary element 13 is a rotary wheel 13.2, as illustrated in FIG. 5. Compared to the rotary arm 13.1, a rotary wheel has the advantage that, in a similar way to the carriage 6 with a plurality of places of deposit 7, it is possible to deposit a plurality of microtitration plates 8 on second resting places 20.2.

The second resting places 20.2 are each formed by a recess 21 which is symmetrical with respect to the radius of the rotary wheel 13.2, is slightly larger than the microtitration plate 8 and has two finger shaped, curved extensions 22. To remove a microtitration plate 8, the rotary wheel 13.2 is rotated above the lifting device 12 arranged below it, in such a way that one of the recesses 21 is located accurately above the microtitration plate 8 lying on the lifting device 12. Then, the bolts 11 are extended and the microtitration plate 8 is lifted through the recess 21 to above the rotary wheel 13.2. The rotary wheel 13.2 is then rotated through an angle α, during which movement the extensions 22 are pivoted around the bolts 11. When the bolts 11 are lowered, the microtitration plate 8 is deposited between a third pin arrangement 24. Between the third pin arrangement 24, there is, in a corresponding manner to the first cutout 19 in the rotary arm 13.1 described in the first exemplary embodiment, a second cutout 25 which is symmetrical with respect to the radius of the rotary wheel 13.2. In a similar manner as with the rotary arm 13.1, the microtitration plate 8 can be deposited on or removed from the rotary wheel 13.2 by means of loading arm 17 or by means of lifting device 12. In the second exemplary embodiment, the rotary wheel 13.2 has four second resting places 20.2 which are arranged at equal angular intervals on the rotary wheel 13.2. The number of second resting places 20.2 can be increased by increasing the diameter of the rotary wheel 13.2.

The three pin arrangements 9, 23 and 24 do not have to be identical. They advantageously each comprise eight conical pins, in each case two of which are arranged on a line which is parallel to the edges of the microtitration plate 8 deposited in the desired position. In order to be able to provide flexible transport for microtitration plates 8 of slightly different external dimensions, it is possible to provide different patterns of holes, into which the suitably fitting pin arrangement is then inserted. As an alternative to pin arrangements, it is also possible to provide corresponding angle brackets or centering blocks with a thread-in chamfer in order for the microtitration plate 8 to be deposited in a defined position.

It is advantageous if the rotation shaft 16 can be displaced automatically. In this way, it is possible, for example, to transfer the microtitration plate 8 from the rotary element 13 to loading arms at different heights which are not themselves vertically adjustable but can only be moved in a single plane. This makes it possible to construct multistory arrangements, which lead to a more compact structure with many additional arrangements.

While the foregoing description and drawings represent the preferred embodiments of the present invention, it will be obvious to those skilled in the art that various changes and modifications may be made therein without departing from the true spirit and scope of the present invention.

What is claimed is:

1. An arrangement for transporting microtitration plates in an automatic handling machine, comprising:
   - at least one linear-transport device, on which a carriage, which has at least one place of deposit for a microtitration plate, is transported in a straight line, under automatic control, between two limit positions;
   - a lifting device with vertically displaceable bolts, by which the microtitration plates can be lifted off or deposited on the carriage;
   - at least one rotary device, in which a rotary element which has at least one resting place for a microtitration plate can be moved, under automatic control, about a fixed rotation shaft; and
   - said rotary device being designed and arranged in such a way with respect to the linear-transport device that the resting place can be rotated between the place of deposit and the microtitration plate which has been lifted and is resting on said bolts, so that the surface centers of gravity of the place of deposit of the resting place and of the microtitration plate lie on a line which is parallel to the bolts;
   - wherein the rotary element is a rotary arm which, at its free end is of plate-like design and has a jaw-shaped recess which allows the rotary arm to pivot about the extended bolts, and which rotary arm has a first cutout which is symmetrical with respect to the axis of the rotary arm and makes it possible to guide a loading arm under the microtitration plate resting on the rotary arm, and which arm has means which guarantee a defined position of the microtitration plate.

2. The arrangement according to claim 1, wherein the rotation shaft is vertically displaceable, in order to allow the microtitration plates to be transferred at various levels.

3. The arrangement according to claim 2, wherein a pin arrangement in rings guarantee a defined position of the microtitration plates by, in each case two pins being arranged on a line which runs parallel to the outer edges of the microtitration plates in their desired position.

4. An arrangement for transporting microtitration plates in an automatic handling machine, comprising:
   - at least one linear-transport device, on which a carriage, which has at least one place of deposit for a microtitration plate, is transported in a straight line, under automatic control, between two limit positions;
   - a lifting device with vertically displaceable bolts, by which the microtitration plates can be lifted off or deposited on the carriage;
   - at least one rotary device, in which a rotary element which has at least one resting place for a microtitration plate can be moved, under automatic control, about a fixed rotation shaft; and
   - said rotary device being designed and arranged in such a way with respect to the linear-transport device that the resting place can be rotated between the place of deposit and the microtitration plate which has been lifted and is resting on said bolts, so that the surface centers of gravity of the place of deposit of the resting place and of the microtitration plate lie on a line which is parallel to the bolts;
   - wherein the rotary element is a rotary wheel, in which each resting place has a recess which is symmetrical with respect to the radius of the rotary wheel makes it possible to lift the microtitration plate resting on the bolts through the rotary wheel and then to rotate the rotary wheel through an angle a, circularly curved extensions of the recess being pivoted about the bolts until the microtitration plate is located above a second cutout, which is likewise symmetrical with respect to the radius of the rotary wheel, makes it possible to guide a loading arm under the microtitration plate resting on the resting place and has means which guarantee a defined position of the microtitration plate.

5. The arrangement according to claim 4, wherein a pin arrangement in rings guarantee a defined position of the microtitration plates by, in each case two pins being arranged on a line which runs parallel to the outer edges of the microtitration plates in their desired position.

* * * * *